United States Patent
Suzuki et al.

(10) Patent No.: US 7,005,532 B2
(45) Date of Patent: Feb. 28, 2006

(54) PROCESS OF PRODUCING ALKOXYSILANES

(75) Inventors: Eiichi Suzuki, Tokyo (JP); Masaki Okamoto, Yokohama (JP); Seitaro Tajima, Nagoya (JP); Hiroshi Suzuki, Nagoya (JP); Katsuyoshi Harada, Tokyo (JP)

(73) Assignee: Toagosei Co., Ltd., Tokyo (JP)

( * ) Notice: Subject to any disclaimer, the term of this patent is extended or adjusted under 35 U.S.C. 154(b) by 0 days.

(21) Appl. No.: 10/489,719

(22) PCT Filed: Sep. 11, 2002

(86) PCT No.: PCT/JP02/09282

§ 371 (c)(1),
(2), (4) Date: Sep. 22, 2004

(87) PCT Pub. No.: WO03/024979

PCT Pub. Date: Mar. 27, 2003

(65) Prior Publication Data

US 2005/0020845 A1    Jan. 27, 2005

(30) Foreign Application Priority Data

Sep. 14, 2001    (JP) .............................. 2001-280537

(51) Int. Cl.
*C07F 7/18* (2006.01)
(52) U.S. Cl. ..................... 556/479; 556/481
(58) Field of Classification Search .............. 556/479, 556/481

See application file for complete search history.

(56) References Cited

U.S. PATENT DOCUMENTS 3,220,972 A  *  11/1965  Lamoreaux ................... 528/15
4,579,965 A  *   4/1986  Kanner et al. ............... 556/479
5,663,400 A       9/1997  Reitmeier et al.
6,858,746 B1  *   2/2005  Giessler et al. ............. 556/481

FOREIGN PATENT DOCUMENTS

EP    0277023 A2  *  8/1988

OTHER PUBLICATIONS

Okamoto, M. et al., "A novel catalyst containing a platinum complex in polyethylene glycol medium supported on silicagel for vapor-phase hydrosily-lation of acetylene with trichlorosilane or tri-methoxysilane", Chem. Commun., Aug. 2002, No. 15, pp. 1634 to 1635.

Hironari Kitani et al., Silica Tantai Hakkin Ganyu Polymer Shokubai o Mochiita Kiso Ryutsu ni yoru Hydrosilyl-ka', Dai 88 Kai Shokubai Toronkai Toronkai A Yokoshu, Sep. 20, 2001, p. 272.

Hironari Kitani et al., "Tanji Hakkin Shokubai o Mochiita Kiso Ryutsukei ni yoru Hydrosilyl-ka", Dai 86 Kai Shokubai Toronkai Toronkai A Yokoshu, Aug. 28, 2000, p. 365.

* cited by examiner

*Primary Examiner*—Porfirio Nazario-Gonzalez
(74) *Attorney, Agent, or Firm*—Sughrue Mion, PLLC

(57) ABSTRACT

An object of the present invention is to provide a process of producing alkoxysilanes, which does not use a chlorosilane as the intermediate raw material, is improved in view of the environment, and is satisfactory with respect to the yield of a desired material.

The present invention is concerned with a process of producing an alkoxysilane including hydrosilylating (A) an organosilicon compound having at least one hydrogen-silicon bond and at least one alkoxy group and (B) an organic compound having a carbon—carbon unsaturated bond in vapor phase in the presence of a mixture containing a hydrosilylation catalyst and a polyalkylene glycol and supported on a carrier, thereby adding hydrogen and silicon of the compound (A) to the carbon—carbon unsaturated bond in the compound (B).

13 Claims, No Drawings

PROCESS OF PRODUCING ALKOXYSILANES

TECHNICAL FIELD

The present invention relates to a process of efficiently producing alkoxysilanes such as alkyl trialoxysilanes, dialkyl dialkoxysilanes, vinyl trialkoxysilanes, vinylalkyl dialkoxysilanes or vinyldialkyl alkoxysilanes. The alkoxysilanes obtained by the present invention can be widely applied as a variety of silane coupling agents and raw materials for insulating thin films and heat resistant materials.

BACKGROUND ART

Alkoxysilanes are useful as a variety of silane coupling agents and raw materials for insulating thin films and heat resistant materials. In particular, in view of the matter that vinyl trialkoxysilanes can be derived into a variety of polymer materials, a demand thereof is high, and processes of producing the same inexpensively and efficiently are being required.

As the industrial production process of alkoxysilanes, the following processes using a chlorosilane as the intermediate raw material are known.

(1) Production Process of Alkoxysilanes Having an Unsaturated Bond:

For example, vinyl trialkoxysilanes are produced by hyrosilylating trichlorosilane and acetylene in the presence of a platinum catalyst to obtain vinyl trichlorosilane as an intermediate raw material and reacting it with an alcohol (for example, see J. Am. Chem. Soc., 68, 2282 (1964)).

This production process is similarly applicable to the production of vinylalkyl dialkoxysilanes or vinyldialkyl alkoxysilanes.

(2) Production Process of Alkoxysilanes Not Having an Unsaturated Bond:

For example, alkyl trialkoxysilanes are produced by reacting an alkyl trichlorosilane with an alcohol.

This production process is similarly applicable to the production of dialkyl dialkoxysilanes, except for using a dialkyl dichlorosilane as the raw material (for example, see German Patent No. 2,800,017 and European Patent No. 107,765).

However, the above production process using the chlorosilane as the (intermediate) raw material involves the following problems.

Large amounts of hydrochloric acid and chlorine-containing compounds are formed as by-products.

For that reason, a purification step of alkoxysilanes is necessary, and complicated operations such as distillation are required.

Further, since hydrochloric acid formed as a by-product corrodes reactors, corrosion-resistant and expensive reactors are required.

As the industrial production process of alkoxysilanes not using a chlorosilane as the intermediate raw material, the following processes by hydrosilylation are known.

(3) Production Process of Alkoxysilanes Having an Unsaturated Bond:

An organosilicon compound having an H—Si bond is reacted with an alkyne compound such as acetylene. As the foregoing organosilicon compound, trialkoxysilanes, alkyl dialkoxysilanes, or dialkyl alkoxysilanes can be used as the raw material.

(4) Production Process of Alkoxysilanes Not Having an Unsaturated Bond:

An organosilicon compound having an H—Si bond is reacted with an olefin compound such as ethylene. As the organosilicon compound, the same compounds as in (3) can be used as the raw material.

However, according to the conventional production processes (3) and (4), the hydrosilylation is carried out in a solvent, and there are encountered the following problems.

A large amount of the solvent as deteriorated due to recycle use must be subjected to incineration.

For that reason, the product cost increases.

Further, carbon dioxide is generated by the incineration, thereby injuring the environment.

As the production process of alkoxysilanes using neither a chlorosilane as the intermediate raw material nor a large amount of a solvent, a method of subjecting an organosilicon compound having an H—Si group and acetylene to hydrosilylation in vapor phase in a loop reactor equipped with a jet nozzle is known (see JP-A-10-59982).

However, even in this method, a small amount of a solvent for forming a jet is necessary, and a special reactor is necessary. Accordingly, further improvement is still required as the inexpensive and efficient production process of alkoxysilanes while taking into consideration the environmental problem.

As the process of producing organosilicon compounds inexpensively and efficiently while prolonging the life of a catalyst, a method is known in which trichlorosilane and acetylene are subjected to hydrosilylation in vapor phase in the presence of a polyethylene glycol solution of hexachloroplatinic(IV) acid supported on a silica gel, thereby obtaining vinyl trichlorosilane in high yield (see $86^{th}$ Catalysis Society Meeting (Part A), Preprint, 4H23, page 365 (September 2000), Tottori).

On review of the subject technology, effectiveness of a variety of catalysts was evaluated, thereby obtaining the following conclusion.

When $H_2PtCl_6$ was dissolved in polyethylene glycol, a lowering of activity even after elapse of 6 hours after start of the reaction was not observed, and the life of a catalyst was prolonged.

The technology presented at the above Catalysis Society Meeting is concerned with hydrosilylation between trichlorosilane and acetylene. However, in the case that an organosilicon compound having a hydrogen-silicon bond but not containing chlorine is used as the raw material, this technology is unclear on whether or not the same high catalytic activity is obtained.

Rather, it may be considered that since the reaction rate of hydrosilylation between a chlorosilane and an organic compound having a carbon—carbon unsaturated bond, the reaction in vapor phase is easy. However, since an organosilicon compound having a hydrogen-silicon bond but not containing a halogen group is low in reactivity, it is generally considered that the efficiency of hydrosilylation in vapor phase is poor.

In the present circumstances, any review is not made on hydrosilylation in vapor phase using an organosilicon compound having a hydrogen-silicone bond but not containing a halogen group as the raw material.

An object of the present invention is to provide a process of producing alkoxysilanes, which does not use a chlorosilane as the intermediate raw material, is improved in view of the environment, and is satisfactory with respect to the yield of a desired material.

DISCLOSURE OF THE INVENTION

In view of the above problems, the present inventors made extensive and intensive investigations. As a result, it has been found that it is extremely effective to conduct hydrosilylation in vapor phase in the presence of a specific catalyst, leading to accomplishment of the present invention.

Specifically, the present invention provides a process of producing an alkoxysilane comprising hydrosilylating (A) an organosilicon compound having at least one hydrogen-silicon bond and at least one alkoxy group and (B) an organic compound having a carbon—carbon unsaturated bond in vapor phase in the presence of a mixture comprising a hydrosilylation catalyst and a polyalkylene glycol and supported on a carrier, thereby adding hydrogen and silicon of the compound (A) to the carbon—carbon unsaturated bond in the compound (B).

BEST MODE FOR CARRYING OUT THE INVENTION

The present invention will be described in detail below.

Raw Material 1 (Organosilicon Compound)

The organosilicon compound (A) used as the raw material in the present invention has at least one hydrogen-silicon bond and at least one alkoxy group.

The organosilicon compound that is preferred as the raw material is one capable of being stably vaporized without causing decomposition during the reaction of the invention and is represented by the following general formula.

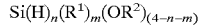

$$Si(H)_n(R^1)_m(OR^2)_{(4-n-m)}$$

(wherein $R^1$ and $R^2$ each represents an alkyl group having 1–4 carbon atoms; n is 1 or 2; m represents an integer of 0–2; and (m+n) is 3 or less).

Preferred organosilicon compounds are as follows:

trimethoxysilane, triethoxysilane, tri-n-propoxysilane, triisopropoxysilane, tri-n-butoxysilane, tri-sec-butoxysilane, triisobutoxysilane, tri-tert-butoxysilane, methyl dimethoxysilane, methyl diethoxysilane, methyl di-n-propoxysilane, methyl diisopropoxysilane, methyl di-n-butoxysilane, methyl di-sec-butoxysilane, methyl diisobutoxysilane, methyl di-tert-butoxysilane, ethyl dimethoxysilane, ethyl diethoxysilane, ethyl di-n-propoxysilane, ethyl diisopropoxysilane, ethyl di-n-butoxysilane, ethyl di-sec-butoxysilane, ethyl diisobutoxysilane, ethyl di-tert-butoxysilane, n-propyl dimethoxysilane, n-propyl diethoxysilane, n-propyl di-n-propoxysilane, n-propyl diisopropoxysilane, n-propyl di-n-butoxysilane, n-propyl di-sec-butoxysilane, n-propyl diisobutoxysilane, n-propyl di-tert-butoxysilane, isopropyl dimethoxysilane, isopropyl diethoxysilane, isopropyl di-n-propoxysilane, isopropyl diisopropoxysilane, isopropyl di-n-butoxysilane, isopropyl di-sec-butoxysilane, isopropyl diisobutoxysilane, isopropyl di-tert-butoxysilane, n-butyl dimethoxysilane, n-butyl diethoxysilane, n-butyl di-n-propoxysilane, n-butyl diisopropoxysilane, n-butyl di-n-butoxysilane, n-butyl di-sec-butoxysilane, n-butyl diisobutoxysilane, n-butyl di-tert-butoxysilane, sec-butyl dimethoxysilane, sec-butyl diethoxysilane, sec-butyl di-n-propoxysilane, sec-butyl diisopropoxysilane, sec-butyl di-n-butoxysilane, sec-butyl di-sec-butoxysilane, sec-butyl diisobutoxysilane, sec-butyl di-tert-butoxysilane, isobutyl dimethoxysilane, isobutyl diethoxysilane, isobutyl di-n-propoxysilane, isobutyl diisopropoxysilane, isobutyl di-n-butoxysilane, isobutyl di-sec-butoxysilane, isobutyl diisobutoxysilane, isobutyl di-tert-butoxysilane, tert-butyl dimethoxysilane, tert-butyl diethoxysilane, tert-butyl di-n-propoxysilane, tert-butyl diisopropoxysilane, tert-butyl di-n-butoxysilane, tert-butyl di-sec-butoxysilane, tert-butyl diisobutoxysilane, tert-butyl di-tert-butoxysilane, trimethylsilane, triethylsilane, tri-n-propylsilane, triisopropylsilane, tri-n-butylsilane, tri-sec-butylsilane, triisobutylsilane, and tri-tert-butylsilane. Of those, trimethoxysilane and triethoxysilane are especially preferable.

Raw Material 2 (Organic Compound Having a Carbon—Carbon Unsaturated Bond)

The organic compound (B) having a carbon—carbon unsaturated bond that is used as the raw material in the present invention is a compound generally called an olefin compound or an alkyne compound. As the olefin compound as referred to herein, any compounds having a carbon—carbon double bond may be used and include monoolefins and diolefins. Although the bonding position of the double bond can be any position, it is preferable that the double bond is present at the end position in view of reactivity.

The preferred olefin compound is a compound having 1–6 carbon atoms, and examples thereof include ethylene, propylene, butylene, butadiene, n-pentene, and hexene. Those compounds can be used alone or as mixtures of two or more thereof. Of those compounds, ethylene, propylene, and butadiene are especially preferable.

Further, as the alkyne compound, any compounds having a carbon—carbon triple bond may be used, and the number and bonding position are not limited. Usually, compounds having one triple bond at the end position are preferable in view of reactivity.

The preferred alkyne compound is a compound having 1–6 carbon atoms, and examples thereof include acetylene, propyne, 1-butyne, 2-butyne, and 1-pentyne. Those compounds can be used alone or as mixtures of two or more thereof. Of those compounds, acetylene is especially preferable.

The olefin compound and alkyne compound each can be used alone or in combination.

Product

The product obtained in the present invention is an alkoxysilane in which hydrogen and silicon of the compound (A) are added to the carbon—carbon unsaturated bond in the compound (B).

Specific compounds are as follows:

trimethoxyethyl silane, ethyl triethoxysilane, ethyl tri-n-propoxysilane, ethyl triisopropoxysilane, ethyl tri-n-butoxysilane, ethyl tri-sec-butoxysilane, ethyl triisobutoxysilane, ethyl tri-tert-butoxysilane, methylethyl dimethoxysilane, methylethyl diethoxysilane, methylethyl di-n-propoxysilane, methylethyl diisopropoxysilane, methylethyl di-n-butoxysilane, methylethyl di-sec-butoxysilane, methylethyl diisobutoxysilane, methylethyl di-tert-butoxysilane, diethyl dimethoxysilane, diethyl diethoxysilane, diethyl di-n-propoxysilane, diethyl diisopropoxysilane, diethyl di-n-butoxysilane, diethyl di-sec-butoxysilane, diethyl diisobutoxysilane, diethyl di-tert-butoxysilane, ethyl-n-propyl dimethoxysilane, ethyl-n-propyl diethoxysilane, ethyl-n-propyl di-n-propoxysilane, ethyl-n-propyl diisopropoxysilane, ethyl-n-propyl di-n-butoxysilane, ethyl-n-propyl di-sec-butoxysilane, ethyl-n-propyl diisobutoxysilane, ethyl-n-propyl di-tert-butoxysilane, ethylisopropyl dimethoxysilane, ethylisopropyl diethoxysilane, ethylisopropyl di-n-propoxysilane, ethylisopropyl diisopropoxysilane, ethylisopropyl di-n-butoxysilane, ethylisopropyl di-sec-butoxysilane, ethylisopropyl diisobutoxysilane, ethylisopropyl di-tert-butoxysilane, ethyl-n-butyl dimethoxysilane, ethyl-n-butyl diethoxysilane, ethyl-n-butyl di-n-propoxysilane, ethyl-n-butyl diisopropoxysilane, ethyl-n-butyl di-n-butoxysilane, ethyl-n-butyl di-sec-butoxysilane, ethyl-n-butyl diisobutoxysilane, ethyl-n-butyl di-tert-butoxysilane, ethyl-sec-butyl dimethoxysilane, ethyl-sec-butyl diethoxysilane, ethyl-sec-butyl di-n-propoxysilane, ethyl-sec-butyl diisopropoxysilane, ethyl-sec-butyl di-n-butoxysilane, ethyl-sec-butyl di-sec-butoxysilane, ethyl-sec-butyl diisobutoxysilane, ethyl-sec-butyl di-tert-butoxysilane, ethylisobutyl dimethoxysilane, ethylisobutyl diethoxysilane, ethylisobutyl di-n-propoxysilane, ethylisobutyl diisopropoxysilane, ethylisobutyl di-n-butoxysilane, ethylisobutyl di-sec-butoxysilane, ethylisobutyl diisobutoxysilane, ethylisobutyl di-tert-butoxysilane, ethyl-tert-butyl dimethoxysilane, ethyl-tert-butyl diethoxysilane, ethyl-tert-butyl di-n-propoxysilane, ethyl-tert-butyl diisopropoxysilane, ethyl-tert-butyl di-n-butoxysilane, ethyl-tert-butyl di-sec-butoxysilane, ethyl-tert-butyl diisobutoxysilane, ethyl-tert-butyl di-tert-butoxysilane, ethyl trimethylsilane, tetraethylsilane, ethyl tri-n-propylsilane, ethyl triisopropylsilane, ethyl tri-n-butylsilane, ethyl tri-sec-butylsilane, ethyl tributylsilane, ethyl tri-tert-butylsilane, vinyl trimethoxysilane, vinyl triethoxysilane, vinyl tri-n-propoxysilane, vinyl triisopropoxysilane, vinyl tri-n-butoxysilane, vinyl tri-sec-butoxysilane, vinyl triisobutoxysilane, vinyl tri-tert-butoxysilane, vinylmethyl dimethoxysilane, vinylmethyl diethoxysilane, vinylmethyl di-n-propoxysilane, vinylmethyl diisopropoxysilane, vinylmethyl di-n-butoxysilane, vinylmethyl di-sec-butoxysilane, vinylmethyl diisobutoxysilane, vinylmethyl di-tert-butoxysilane, vinylethyl dimethoxysilane, vinylethyl diethoxysilane, vinylethyl di-n-propoxysilane, vinylethyl diisopropoxysilane, vinylethyl di-n-butoxysilane, vinylethyl di-sec-butoxysilane, vinylethyl diisobutoxysilane, vinylethyl di-tert-butoxysilane, vinyl-n-propyl dimethoxysilane, vinyl-n-propyl diethoxysilane, vinyl-n-propyl di-n-propoxysilane, vinyl-n-propyl diisopropoxysilane, vinyl-n-propyl di-n-butoxysilane, vinyl-n-propyl di-sec-butoxysilane, vinyl-n-propyl diisobutoxysilane, vinyl-n-propyl di-tert-butoxysilane, vinylisopropyl dimethoxysilane, vinylisopropyl diethoxysilane, vinylisopropyl di-n-propoxysilane, vinylisopropyl diisopropoxysilane, vinylisopropyl di-n-butoxysilane, vinylisopropyl di-sec-butoxysilane, vinylisopropyl diisobutoxysilane, vinylisopropyl di-tert-butoxysilane, vinyl-n-butyl dimethoxysilane, vinyl-n-butyl diethoxysilane, vinyl-n-butyl di-n-propoxysilane, vinyl-n-butyl diisopropoxysilane, vinyl-n-butyl di-n-butoxysilane, vinyl-n-butyl di-sec-butoxysilane, vinyl-n-butyl diisobutoxysilane, vinyl-n-butyl di-tert-butoxysilane, sec-butyl dimethoxysilane, vinyl-sec-butyl diethoxysilane, vinyl-sec-butyl di-n-propoxysilane, vinyl-sec-butyl diisopropoxysilane, vinyl-sec-butyl di-n-butoxysilane, vinyl-sec-butyl di-sec-butoxysilane, vinyl-sec-butyl diisobutoxysilane, vinyl-sec-butyl di-tert-butoxysilane, vinylisobutyl dimethoxysilane, vinylisobutyl diethoxysilane, vinylisobutyl di-n-propoxysilane, vinylisobutyl diisopropoxysilane, vinylisobutyl di-n-butoxysilane, vinylisobutyl di-sec-butoxysilane, vinylisobutyl diisobutoxysilane, vinylisobutyl di-tert-butoxysilane, vinyl-tert-butyl dimethoxysilane, vinyl-tert-butyl diethoxysilane, vinyl-tert-butyl di-n-propoxysilane, vinyl-tert-butyl diisopropoxysilane, vinyl-tert-butyl di-n-butoxysilane, vinyl-tert-butyl di-sec-butoxysilane, vinyl-tert-butyl diisobutoxysilane, vinyl-tert-butyl di-tert-butoxysilane, vinyl trimethylsilane, vinyl triethylsilane, vinyl tri-n-propylsilane, vinyl triisopropylsilane, vinyl tri-n-butylsilane, vinyl tri-sec-butylsilane, vinyl triisobutylsilane, and vinyl tri-tert-butylsilane. Of these compounds, vinylethyl diethoxysilane is especially preferable.

Hydrosilylation Catalyst

Although the hydrosilylation catalyst in the present invention is not particularly limited so far as it functions as a catalyst for the hydrosilylation, catalysts containing Group 8 metal are preferable.

Preferred examples of the Group 8 metal include iron, cobalt, nickel, palladium, and platinum, and catalysts containing such a Group 8 metal of the Element Table can be used. Platinum-containing catalysts are especially preferable.

Specific examples of preferred platinum-containing catalysts include chloroplatinic acid; platinum compounds such as complexes of chloroplatinic acid with an alcohol, an aldehyde, a ketone, etc.; platinum complexes such as platinum-olefin complexes [for example, $Pt(CH_2=CH_2)_2(PPh_3)$ and $Pt(CH_2=CH_2)_2Cl_2$], platinum-vinyl siloxane complexes [for example, $Pt\{(vinyl)Me_2SiOSiMe_2(vinyl)\}$ and $Pt\{Me(vinyl)\text{-}SiO\}_4$], platinum-phosphine complexes [for example, $Pt(PPh_3)_4$ and $Pt(PBu_3)_4$], and platinum-phosphite complexes [for example, $Pt\{P(OPh)_3\}_4$] (wherein Ph represents a phenyl group, and Bu represents a butyl group). Further, dicarbonyldichloroplatinum, platinum-hydrocarbon composite bodies described in U.S. Pat. Nos. 3,159,601 and 3,159,662 to Ashby, and platinum-alcoholate catalysts described in U.S. Pat. No. 3,220,972 to Lamoreaux can be enumerated. Furthermore, platinum chloride-olefin composite bodies described in U.S. Pat. No. 3,516,946 to Modic are also effective in the present invention. These compounds may be used alone or as mixtures of two or more thereof. Platinum complexes having at least one $NH_3$ as a ligand are especially preferable from the standpoint of reaction activity.

Specific examples of platinum complexes having at least one $NH_3$ as a ligand are as follows:

ammine(ethylamine)tetrachloroplatinum(IV), ammine(ethylenediamine)pyridineplatinum(II) salts, amminedichloro(ethylenediamine)nitroplatinum(IV) salts, amminedichloro(pyridine)platinum(II), amminedibromo(ethylene)platinum(II), amminetrichloroplatinic(II) acid salts, amminetris(pyridine)platinum(II) salts, amminepentachloroplatinic(IV) acid salts, diammineanilinechloroplatinum(II) salts, diammineoxalatoplatinum(II), diamminecarbonylchloroplatinum(II) salts, diamminechloro(thioether)platinum(II) salts, diamminediaquaplatinum(II) salts, diamminedicarbonylplatinum(II) salts, diamminedichloroplatinum(II), diaminedinitratoplatinum(II), diamminedinitroplatinum(II), diaminedihydroxodinitroplatinum(IV), diamminedihydroxoplatinum(II), diamminedihydroxobis(nitrato)platinum(IV), diaminedibromoplatinum(II), diamminetetrakis(nitrato)platinum(IV), diamminetetrachloroplatinum(IV), diamminebis(ethylamine)platinum(II) salts, diamminebis(sulfito)platinic(II) acid salts, diamminebis(thiocyanato)platinum(II), diamminebis(hydrazine)platinum(II) salts, dimminebis(hydrogenoxalato)platinum(II), diamminebis(phosphine)platinum(II), triammineaquaplatinum(II) salts, triamminechloroplatinum(II) salts, triamminetrichloroplatinum(IV) salts, triamminenitroplatinum(II) salts, triamminehydroxylamineplatinum(II) salts, tetraamminechloronitratoplatinum(IV) salts, tetraamminechlorohydroxoplatinum(IV) salts, tetraammineplatinum(II) salts, tetraamminedichloroplatinum(IV) salts, tetraamminedihydroxoplatinum(IV) salts, tetraamminedibromoplatinum(IV) salts, and tetraamminesulfatoplatinum(IV) salts. Of those, tetraammineplatinum (II) salts are preferable, and tetraammineplatinum(II) chloride is especially preferable.

Polyalkylene Glycol

The polyalkylene glycol in the present invention has an ability to dissolve or disperse the hydrosilylation catalyst therein, thereby providing the place where the organosilicon compound (A) and the organic compound (B) having a carbon—carbon unsaturated bond as the raw materials come into contact with each other. The polyalkylene glycol is preferably one which does not cause decomposition or vaporization in the temperature range of 100–250° C. Specific examples are as follows:

polyethylene glycol, etherified products of polyethylene glycol, esterified products of polyethylene glycol, urethanized products of polyethylene glycol, polypropylene glycol, etherified products of polypropylene glycol, esterified products of polypropylene glycol, urethanized products of polypropylene glycol, polytetramethylene glycol, etherified products of polytetramethylene glycol, esterified products of polytetramethylene glycol, urethanized products of polytetramethylene glycol, poly(oxyethylene-oxymethylene)copolymers, and poly(oxyethylene-oxypropylene)copolymers.

Of those, polyethylene glycol is especially preferable in view of the ability to dissolve the hydrosilylation catalyst.

Carrier

The carrier for supporting a mixture of the hydrosilylation catalyst and the polyalkylene glycol can be any carrier so long as it is inert against the hydrosilylation catalyst and the polyalkylene glycol in the temperature range of 100–250° C. and can be used in vapor phase reaction as a carrier.

Preferred examples of the carrier include single metal oxides such as alumina, silica, titania, magnesia or zirconia, zeolite, active carbon, diatomaceous earth, and cordierite. Of those, silica is preferable, and silica gel is especially preferable.

Supporting Method of Hydrosilylation Catalyst and Polyalkylene Glycol

The method of supporting a mixture comprising a hydrosilylation catalyst-containing solution and a polyalkylene glycol on a carrier is not particularly limited. For example, it is easily achieved by impregnating and supporting the mixture on the carrier.

In mixing the hydrosilylation catalyst and the polyalkylene glycol, the mixing becomes easy by using a solvent such as water or alcohols. The solvent may become an obstacle in smoothly advancing the hydrosilylation. Accordingly, an operation in which prior to the hydrosilylation, the carrier-supported mixture comprising a hydrosilylation catalyst and a polyalkylene glycol is heated as pre-treatment, thereby removing water or the alcohol, is employed. The temperature of the pre-treatment may be a temperature at which the solvent of the catalyst solution can be sufficiently removed and is chosen within the temperature range of 70–250° C. It is preferable to conduct the pre-treatment while passing an inert gas in the reaction system. The inert gas is not particularly limited so far as it does not react with the raw materials, product and catalyst. Examples include nitrogen, argon, and helium.

Hydrosilylation

The hydrosilylation in the present invention is carried out after the pre-treatment by supplying the organosilicon compound having at least one hydrogen-silicon bond and at least one alkoxy group and the organic compound having a carbon—carbon unsaturated bond in the gaseous state in the presence of the carrier-supported mixture comprising a hydrosilylation catalyst and polyethylene glycol.

The supply molar ratio of the organosilicon compound to the compound having a carbon—carbon unsaturated bond is preferably 1/1–1/50, more preferably 1/1–1/20, and further preferably 1/1–1/10.

While supplying, the reaction temperature is preferably 70–250° C., and especially preferably 100–180° C., in order to prevent decomposition or vaporization of the polyalkylene glycol due to excessive heating.

The supply rate of the raw materials into the reaction system is preferably 1–50 ghmol$^{-1}$, and more preferably 5–30 ghmol$^{-1}$, in terms of the contact time per gram of the carrier supporting the mixture comprising a hydrosilylation catalyst and a polyalkylene glycol. If the supply rate exceeds 50 ghmol$^{-1}$, the unreacted raw materials increase, and a lowering of the conversion results, which are not economical. If it is too small, the conversion may lower. The raw material may be supplied alone or after dilution with an inert gas. However, in the case that an alkyne compound is used as the raw material, it is preferable to supply it after dilution with an inert gas for the purpose of securing safety. The inert gas has a function to eliminate oxygen that injures the life of the catalyst. The concentration of residual oxygen in the reaction system is preferably 1.0% or lower, more preferably 0.5% or lower, and further preferably 0.3% or lower. If the concentration of residual oxygen exceeds 1.0%, a lowering of the conversion of the organosilicon compound having a hydrogen-silicon bond and an alkoxy group results, and therefore, such is not preferable.

The hydrosilylation in the present invention is carried out in the vapor phase system.

The reaction method may be either one of a batch type in which all of the raw materials and the catalyst are charged from the beginning, or a continuous type in which the raw materials and the catalyst are continuously charged during the reaction.

A vibration mode in which the reaction is carried out while vibrating all of the raw materials and the catalyst; a moving bed mode in which the reaction is carried out while moving the raw materials and the catalyst by vibration or a physical force; a fixed bed mode in which the reaction is carried out upon fixing the catalyst; or a fluidized bed mode may also be employed. In any of those types, all of the raw materials are supplied as gases into the reaction system. Although the supply is generally carried out continuously, it can be carried out intermittently.

The reaction of the present invention may be carried out either at atmospheric pressure or under pressure, but it is preferable to conduct it at atmospheric pressure from the standpoints of safety and costs of reactor.

In the present invention, the overall reaction pressure is from atmospheric pressure to 10 MPa, and preferably 1–5 MPa. If the overall reaction pressure exceeds 10 MPa, the high-boiling product is not smoothly distilled away from the reaction system, and the conversion of the desired material lowers, whereas if it is a reduced pressure, the conversion of the organosilicon compound (A) as the raw material lowers, and therefore, such is not economical.

The partial pressure of the organosilicon compound (A) in the present invention is, for example, 0.001–5 MPa, and preferably 0.01–1 MPa. If the partial pressure is less than 0.001 MPa, the selectivity of the desired material lowers, whereas if it exceeds 1 MPa, the conversion of the organosilicon compound (A) lowers, and therefore, such is not economical.

The partial pressure of the organic compound (B) having a carbon—carbon unsaturated bond in the present invention is, for example, 0.001–5 MPa, and preferably 0.01–1 MPa. If the partial pressure is less than 0.001 MPa, the selectivity of the desired material lowers, whereas if it exceeds 1 MPa, the conversion of the organic compound having a carbon—carbon unsaturated bond lowers, and therefore, such is not economical.

The hydrosilylation in the present invention is a reaction in which the unsaturated bond in the organic compound (B) of an equivalent amount to the equivalent amount of the hydrogen-silicon bond in the organosilicon compound (A) participates. To efficiently obtain the desired material, it is preferable that the organic compound (B) is present excessively as compared with the stoichiometric formulation.

The reaction product liquid according to the reaction method of the present invention contains a high-concentration alkoxysilane and also contains small amounts of by-products such as tetraalkoxysilanes and the unreacted organosilicon compound (A) and organic compound (B) having a carbon—carbon unsaturated bond, but the organosilicon compound as the desired material can be easily separated and obtained from this reaction product liquid by distillation or other customary manners. Incidentally, in the present description, the selectivity of the desired material and the conversion of the organosilicon compound (A) are values calculated in the following Examples.

With respect to the material quality of a reactor of the invention, quartz tubes, glass tubes, metal tubes, and others can be used without particularly limitations. However, it is preferable that the structure of the reactor is one equipped with inlets for introducing the organosilicon compound (A) and the organic compound (B) having a carbon—carbon unsaturated bond, heating and cooling units, and an outlet of the product and having an airtight structure.

EXAMPLES

The present invention will be specifically described below with reference to the following Examples.

Example 1

A tetraammnineplatinum(II) dichloride aqueous solution and polyethylene glycol (hereinafter abbreviated as "PEG") were mixed and supported on a silica gel. An atmospheric fixed bed flow system reactor was used for reaction. Pre-treatment was carried out by heating in a helium gas stream at 150° C. for 1 hour. Thereafter, the reaction temperature was fixed at 150° C., and partial pressures of gases to be flown in the reactor were adjusted at 44 kPa for acetylene, 11 kPa for trimethoxysilane, and 46 kPa for helium, respectively. The product was identified by GC-MS and quantitatively determined by gas chromatography. The conversion of trimethoxysilane, the selectivity of vinyl trimethoxysilane, and the yield of vinyl trimethoxysilane were defined by the following equations.

Conversion of trimethoxysilane={[(supply rate of trimethoxysilane)−(rate of trimethoxysilane at reaction tube outlet)]/(supply rate of trimethoxysilane)}×100 (1)

Selectivity of vinyl trimethoxysilane={(rate of vinyl trimethoxysilane at reaction tube outlet)/[(supply rate of trimethoxysilane)−(rate of trimethoxysilane at reaction tube outlet)]}×100 (2)

Yield of vinyl trimethoxysilane=[(rate of vinyl trimethoxysilane at reaction tube outlet)/(supply rate of trimethoxysilane)]×100 (3)

The reaction was carried out while adjusting the contact time at 13.8 ghmol$^{-1}$. As a result, the convention of trimethoxysilane was 70%, the selectivity of vinyl trimethoxysilane was 94%, and the yield of vinyl trimethoxysilane was 67%, at a flow time of 6 hours.

The reaction conditions of this Example and the subsequent Examples and Comparative Example are as follows.

Catalyst: Pt(NH$_3$)$_4$Cl$_2$/PEG/SiO$_2$ (Pt: 0.5 wt %)
Reaction temperature: 423 K
W/F: 7 to 20.7 ghmol$^{-1}$
C$_2$H$_2$: 44 kPa
HSi(OCH$_3$)$_3$ or HSiCl$_3$: 11 kPa

Examples 2

The reaction was carried out in the same manner as in Example 1, except for changing the contact time to 7 ghmol$^{-1}$. As a result, the convention of trimethoxysilane was 54%, the selectivity of vinyl trimethoxysilane was 94%, and the yield of vinyl trimethoxysilane was 51%, at a flow time of 6 hours.

Example 3

The reaction was carried out in the same manner as in Example 1, except for changing the contact time to 20.7 ghmol$^{-1}$. As a result, the convention of trimethoxysilane was 86%, the selectivity of vinyl trimethoxysilane was 97%, and the yield of vinyl trimethoxysilane was 83%, at a flow time of 6 hours.

Comparative Example 1

The reaction was carried out under the same synthesis condition as in Example 1, except for changing the reactive substrate to trichlorosilane. That is, a tetraammnineplatinum (II) dichloride aqueous solution and PEG were mixed and supported on a silica gel. An atmospheric fixed bed flow system reactor was used for reaction. Pre-treatment was carried out upon heating in a helium gas stream at 150° C. for 1 hour. Thereafter, the reaction temperature was fixed at 150° C., and partial pressures of gases to be flown in the reactor were adjusted at 44 kPa for acetylene, 11 kPa for trichlorosilane, and 46 kPa for helium, respectively. The product was identified by GC-MS and quantitatively determined by gas chromatography. The conversion of trichlorosilane, the selectivity of vinyl trichlorosilane, and the yield of vinyl trimethoxysilane were defined by the following equations.

Conversion of trichlorosilane={[(supply rate of trichlorosilane)−(rate of trichlorosilane at reaction tube outlet)]/(supply rate of trichlorosilane)}×100 (1)

Selectivity of vinyl trichlorosilane={(rate of vinyl trichlorosilane at reaction tube outlet)/[(supply rate of trichlorosilane)−(rate of trichlorosilane at reaction tube outlet)]}×100 (2)

Yield of vinyl trichlorosilane=[(rate of vinyl trichlorosilane at reaction tube outlet)/(supply rate of trichlorosilane)]×100 (3)

The reaction was carried out while adjusting the contact time at 13.8 ghmol$^{-1}$. As a result, the convention of trichlorosilane was 61%, the selectivity of vinyl trichlorosilane was 85%, and the yield of vinyl trichlorosilane was 52%, at a flow time of 6 hours.

As is clear from the Examples of the present invention, it is understood that the activity of the catalyst endures for an extremely long period of time.

Further, when Example 1 is compared with Comparative Example 1, it should be surprised that the alkoxysilane is higher in conversion and selectivity than the chlorosilane that has been considered to have higher activity and that the desired vinyl trialkoxysilane is obtained in high yield.

While the invention has been described in detail and with reference to specific embodiments thereof, it will be apparent to one skilled in the art that various changes and modifications can be made therein without departing from the spirit and scope thereof.

This application is based on a Japanese patent application filed Sep. 14, 2001 (Japanese Patent Application No. 2001-280537), the contents of which are incorporated therein and made hereof by reference.

INDUSTRIAL APPLICABILITY

According to the production process of the present invention, since a chlorosilane is not used as the intermediate raw material, and an organic solvent as in the liquid phase method is not used, the environment is never injured.

Further, since no organic solvent is used, it is easy to separate and obtain the desired organosilicon compound from the reaction product liquid.

Moreover, since the reaction proceeds at a high selectivity without using a specific reactor, the production efficiency is high, and the process is useful as an inexpensive process.

What is claimed is:

1. A process of producing an alkoxysilane, the process comprising:

performing a pre-treatment comprising supporting a solution comprising a solvent, a hydrosilylation catalyst and a polyalkylene glycol on a carrier, and heating the carrier having the solution supported thereon at a temperature of 70–250° C. to remove the solvent, thereby preparing a mixture comprising the carrier having the hydrosilylation catalyst and the polyalkylene glycol supported thereon; and hydrosilylating, in vapor phase, (A) an organosilicon compound having at least one hydrogen-silicon bond and at least one alkoxy group and (B) an organic compound having a carbon—carbon unsaturated bond in the presence of the mixture prepared above, thereby adding hydrogen and silicon of the compound (A) to the carbon—carbon unsaturated bond in the compound (B).

2. The process of producing an alkoxysilane as claimed in claim 1, wherein the organosilicon compound (A) is represented by the following general formula:

$$Si(H)_n(R^1)_m(OR^2)_{(4-n-m)}$$

(wherein $R^1$ and $R^2$ each represents an alkyl group having 1–4 carbon atoms; n is 1 or 2; m represents an integer of 0–2; and (m+n) is 3 or less).

3. The process of producing an alkoxysilane as claimed in claim 1, wherein the organic compound (B) is an olefin compound or an alkyne compound.

4. The process of producing an alkoxysilane as claimed in claim 3, wherein the olefin compound is a compound having 2–6 carbon atoms.

5. The process of producing an alkoxysilane as claimed in claim 3, wherein the alkyne compound has one triple bond and further has 2–6 carbon atoms.

6. The process of producing an alkoxysilane as claimed in claim 1, wherein the hydrosilylation catalyst is a catalyst containing the Group 8 metal.

7. The process of producing an alkoxysilane as claimed in claim 6, wherein the hydrosilylation catalyst is a platinum complex having at least one $NH_3$ as a ligand.

8. The process of producing an alkoxysilane as claimed in claim 1, wherein the polyalkylene glycol is one which does not cause decomposition or vaporization in the temperature range of 100–250° C.

9. The process of producing an alkoxysilane as claimed in claim 1, wherein the carrier is inert against the hydrosilylation catalyst and the polyalkylene glycol in the temperature range of 100–250° C.

10. The process of producing an alkoxysilane as claimed in claim 1, wherein the hydrosilylation is carried out at a temperature of 70–250° C.

11. The process of producing an alkoxysilane as claimed in claim 1, wherein the overall reaction pressure is from atmospheric pressure to 10 MPa.

12. The process of producing an alkoxysilane as claimed in claim 1, wherein the organosilicon compound (A) has a partial pressure of 0.001–5 MPa.

13. The process of producing an alkoxysilane as claimed in claim 1, wherein the organic compound (B) has a partial pressure of 0.001–5 MPa.

* * * * *